(12) United States Patent
Madou

(10) Patent No.: US 6,790,599 B1
(45) Date of Patent: Sep. 14, 2004

(54) MICROFLUIDIC DEVICES AND MANUFACTURE THEREOF

(75) Inventor: Marc J. Madou, Columbus, OH (US)

(73) Assignee: Microbionics, Inc., Redwood City, CA (US)

(*) Notice: Subject to any disclaimer, the term of this patent is extended or adjusted under 35 U.S.C. 154(b) by 727 days.

(21) Appl. No.: 09/615,159

(22) Filed: Jul. 13, 2000

Related U.S. Application Data (60) Provisional application No. 60/144,156, filed on Jul. 15, 1999.

(51) Int. Cl.[7] .................................................. G03F 7/00
(52) U.S. Cl. .................. 430/320; 430/311; 430/312; 430/313; 430/322; 430/323; 430/328; 430/396
(58) Field of Search ............................... 430/311, 312, 430/313, 320, 322, 323, 328, 396

(56) References Cited

U.S. PATENT DOCUMENTS

| | | | | |
|---|---|---|---|---|
| 3,772,101 A | * | 11/1973 | Chumbres et al. | ............ 216/18 |
| 4,765,864 A | * | 8/1988 | Holland et al. | ............... 438/49 |
| 5,130,263 A | * | 7/1992 | Possin et al. | ............... 438/159 |
| 2002/0108860 A1 | * | 8/2002 | Staats | ......................... 204/601 |

* cited by examiner

*Primary Examiner*—Nicole Barreca
(74) *Attorney, Agent, or Firm*—Corwin R. Horton (57) ABSTRACT

Planar microfluidic devices are laminate structures having a matrix layer at an upper side laminated at an interface to a lower substrate layer. The structure has one or more cavities extending from the upper side to the interface. A membrane is laminated on the upper side of the structure thereby to form a fluid barrier for the cavities. Devices for use as electrochemical sensors further include an electrode at the laminate structure interface below the matrix layer cavity and a well through the substrate layer below the electrode for electrical communication.

10 Claims, 5 Drawing Sheets

MICROFLUIDIC DEVICES AND MANUFACTURE THEREOF

This application claims the benefit of provisional application No. 60/144,156, filed Jul. 15, 1999.

BACKGROUND OF THE INVENTION

This invention relates to planar microfluidic devices and their manufacture. Microfluidic devices have a wide range of existing and potential uses in various arts. Of particular importance are microfluidic devices for use as electrochemical microsensors for chemical detection and measurement, especially in biochemical applications such as in medicine. In order to succeed in the point of care market, the biosensor systems must meet their application needs. Planar electrochemical sensors with microelectronic production techniques are known as an elegant approach to meet these requirements. Due to the batch processing and high precision of microelectronic techniques, the miniaturized planar sensors have major advantages including small dimension, low cost per sensor, high reproducibility and the possibility of smart sensor realizations. In the past few years, a number of mnicro-fabricated sensors have been designed and developed by microelectronic techniques. These sensors are usually made on silicon and include integrated electronic elements. The are usable for detecting various ions as well as gases. However, in these cases, silicon is only a substrate and does not play any role in the sensing mechanism itself. There also exist some problems concerning the final package of the sensors because a chemical sensor on an insulating substrate is almost always easier to package than on a piece of silicon with conductive edges in need of insulation. Moreover, many chemical sensor materials are incompatible with IC processing; therefore the very point of using silicon is forfeit for many chemical sensors. Lately, flexible polyimide film (Kapton) has been used as a substrate in microfabricated planar sensor arrays. Photolithography and sputtering technologies are used in the fabrication of the sensor arrays. These sensor arrays have shown good analytical properties in-vivo measurements and solved the problems with respect to membrane optimization, adhesion of membrane to its substrate, etc., but the sputtering process causes the fabrication of sensors to be expensive and time consuming.

As for the configuration of these sensors, the sensor sites and their electrical contacts are on the same side of the substrate. This makes the fabrication of multi-purpose sensor arrays more complicated with a lower production yield. In order to make disposable micro-electrochemical sensors, we believe an elegant approach can be realized by merging IC and screen printing process from silicon wafers to large sheets of dry photoresist films. A modular approach is preferred since there are no electronics on the chip and one only wants to fabricate an array of chemical sensors. This modular approach enables the independent development of different sensors, obviates many compatibility issues, and increases the manufacturing yield dramatically.

At the same time, microfluidic devices are increasingly used in applications for drug discovery and diagnostic area. By using the precise control of flow in microchannels to larger fluidic components, the mixing and the partition of the fluidics with very small samples can be realized. A wide variety of fluidic processes can be carried out with different flow speeds in a combination of pressure-dependent and pressure independent valves. The current method of manufacturing for microfluidics is using a conventional LIGA process for anisotropically etching the microchannels in the silicon wafer with high aspect ratio. Silicon bonding technology is also needed to make a buried channel. However, since the LIGA process needs X-ray sources, which is very expensive, it is difficult to make a cheap disposable microfluidic platform with the conventional approach.

SUMMARY OF THE INVENTION

This invention relates to a new design and fabrication process for microfluidic devices including miniaturized electrochemical sensors. The invention provides microfluidic structures that may be processed and adapted for a wide variety of end uses. In this new design, identical devices, such as miniaturized electrochemical sensors, may be fabricated on sheets of a non-silicon material substrate by a batch, modular-manufacturing methodology. The modular structures each may have one or more microchambers. The microchambers of these structures may be processed while in sheet form appropriately for the end use contemplated. Microchambers of modular structures intended for use as sensors or reference electrodes may be charged with electrolytic media or analytes appropriate to the desired sensor or electrode end use. The individual devices may then separated from the sheet and then integrated into appropriate combinations or systems, such as multiple analyte sensor arrays, using pick and place technology. By fabricating identical miniaturized devices on a single large sheet of substrate the yield substantially increases over conventional substrates.

In this invention microfluidic devices are fabricated by a low cost methodology utilizing negative photoresists as a matrix for these devices. A laminate is formed comprising a negative photoresist matrix layer on a non-silicon support layer. The negative matrix photoresist layer is exposed to radiation through a mask that defines the cavities or wells for the desired microfluidic chambers to thereby fix the photoresist layer at exposed areas and leave this layer unfixed at the masked areas. The matrix photoresist is then developed to remove the photoresist layer at the unfixed areas to thereby form the cavities for the microfluidic devices. A membrane is applied at the surface of the matrix photoresist layer to enclose the wells and form the desired microfluidic chambers. The membrane is provided with one or more small holes or pores at the chambers or channels to provide fluid communication with the chambers to and from the outside, as appropriate to the end use of the devices.

In one feature of the invention, a preformed or "dry" negative photoresist layer is applied to the surface of the matrix photoresist layer as a membrane to cover the cavities. Following its application the covering photoresist is irradiated to fix it to a durable and permanent state. Where applicable, the covering photoresist layer may be exposed to radiation through a mask that defines fluid communication holes, at chamber locations, appropriate to the end use of the microfluidic devices. The second photoresist layer is then developed to form the fluid communication holes through the second photoresist to the chambers. However, without regard to its normal intended function as a photoresist to form a layer with cavities or other desired discontinuities, it has been discovered that application of a dry photoresist to cover the cavities in the matrix layer, as described, is uniquely advantageous. The dry photoresist in this application has been found to bond strongly to the matrix layer without migrating into and clogging the wells, channels and other cavities in the matrix layers for the microfluidic device, as experienced with other types of covering materials.

In another feature of this invention important to microfluidic devices for use as sensors a pre-formed negative photoresist is employed as the support layer for the matrix photoresist layer. In this embodiment, a photo-opaque conductive material, such as silver, is applied to the surface a self-supporting negative photoresist film in discrete spots to form an electrode at each location at which a sensor is to be formed. A negative photoresist matrix layer is applied to the support layer at the side bearing the electrodes to form a laminate in which the electrodes are at the interface of the matrix and support layers. The laminate is exposed to radiation at the matrix layer side while a mask is aligned with each electrode of a size to define the desired cavity for a microfluidic chamber over the electrode but having a span smaller than that of the electrode. The matrix photoresist is thereby fixed across the unmasked surface and remains unfixed at the area below the mask and the substrate photoresist is thereby fixed across its span except for the area below the electrode. Both the matrix photoresist and substrate photoresist are then developed to remove the photoresist layer at the unfixed areas. Wells are thus formed in both the matrix layer and in the substrate layer that extend to the electrodes at the interface therebetween. A membrane may then be applied at the surface of the matrix photoresist layer to enclose the cavities and form the desired microfluidic chambers. The membrane may be provided with one or more small holes or pores at the chambers or channels to provide fluid communication with the chambers to and from the outside, as appropriate to the end use of the devices. The wells in the substrate layer may be employed for electrical communication with the electrodes of the sensors. For this purpose each well may receive an electrical contact pin for contacting the electrode.

In yet another feature of the invention sensors are integrated into arrays in biomodules having fluidic communication channels to the individual sensors. An array of sensors is arranged on a biomodule substrate and a cover arranged across the substrate over sensors which is provided with fluid communication ports to the outside and internal channels above the sensors to provide fluid communication each sensor and the external ports. A preformed negative photoresist may be applied to the biomodule substrate for the cover and then irradiated to fix the photoresist. Internal pillars or walls, preferably also by photoresist application, may be applied to the biomodule substrate, prior to application to the cover, to serve as a bridge to support the cover above the sensors, thereby to form a common communication chamber over the sensors.

BRIEF DESCRIPTION OF THE DRAWINGS

The invention will be better understood by reference to the figures of the drawings wherein like numbers denote like parts throughout and wherein.

DETAILED DESCRIPTION OF THE PREFERRED EMBODIMENT

The following description illustrates the manner in which the principles of the invention are applied but is not to be construed as limiting the scope of the invention.

The present invention provides microfluidic devices structures that may include one or more microchambers within a matrix of negative photoresist. In these structures the negative photoresist is thus used as a structural material for the devices. This design enables the microfluidic devices to be produced at low cost, as compared with silicon-based microfluidic structures, by batch, modular-manufacturing methodology. With this methodology identical miniaturized fluidic devices may be fabricated on a single large sheet with a yield substantially increased over conventional substrates. The individual devices may then be separated and used individually or placed in arrays, such as to produce multiple analyte sensor arrays, using pick and place technology.

In this invention the fluidic devices are formed in a sheet of negative photoresist which serves as the matrix. Negative photoresists, as contemplated in this invention, constitute a film or sheet of material, usually polymeric, that is sensitive to appropriate radiation including radiation in the visible range, of shorter wave length, such as x rays or charged particle radiation. Prior to radiation exposure the material is susceptible to erosion by chemical, solvent or other means and is typically soft. Through exposure of the material to radiation the material will become fixed, that is, harden to a more durable and rigid state. Negative photoresists may be employed in this invention as preformed sheets. So-called "dry" photoresist sheets or films are typically available with peelable cover sheets such as polyolefin or Mylar films to protect the photoresist surfaces, which may be tacky or subject to oxidation. Such materials include photosensitive polyimide-based sheets such as, Pyralux PC 1025 produced by Dupont, and Riston 4600.

As will be described, in this invention negative photoresists may also be formed in situ, as a layer or coating, e.g. from a solvent-based resist formulation that is cast onto the surface of a substrate layer, such as SU-8 photoresists, including SU-8-25, and Pyralin PI2721.

In this invention the negative photoresist which is to serve as the matrix for microfluidic components is cast or laminated as a preformed sheet onto a substrate, layer, preferably a non-conductive self-supporting sheet, typically of a polymeric material. However, a wide variety of substrates may be employed, including polycarbonate, silicon sheets. In important forms of the invention the substrate layer may itself be a preformed negative photoresist, as will be discussed.

The microfluidic devices incorporated in the negative photoresist matrix layer may take a wide variety of forms. They include devices and components of devices for measuring pressure or pH, drug delivery, sensing chemicals, either in gas or liquid form. They may be a complete chemical diagnostic system or chemical reservoirs or reaction chambers and associated channels for such systems. Other devices may include micronozzles for spinnerets, etc, filters, fluidic amplifiers, valves and pumps. One or more fluidic chamber is common to these devices, and these may include channels for communication between chambers and/ or to regions outside of the device. The various microchambers of these devices may be incorporated into the negative photoresist matrix layer of the microfluidic device structures of this invention as will be first described with reference to FIGS. 1 through 4. As appropriate, communication conduits, such as channels, openings, pores or the like in the matrix layer or in covering membranes on the matrix layer are provided for fluid communication between the microchambers and other components in the matrix and/or to regions outside the device. To serve as a matrix for the microfluidic elements, the negative photoresist matrix layer has a thickness desirably of at least 2 microns and preferably at least 35 microns. Typically the matrix layer will have a thickness of between 35 and 600 microns. For most applications the matrix layer will have a thickness 600 microns or less.

The various individual steps in the fabrication of the microfluidic structures of this invention, per se, are well known in the art. These include photolithography and in particular irradiation by contact or projection printing, use of photomasks and developing of irradiated photoresists, silk screening and other printing techniques, lamination of preformed negative photoresists to substrates, spinning and other techniques for applying a solvent-based photoresist layer, and design of specific microfluidic devices and sensors for specific applications, Literature available on these subjects include the text *Fundamentals of Microfabrication*, M. Madou, CRC Press, Boca Raton, 1997, the disclosures of which are incorporated herein by reference.

Figure 1:
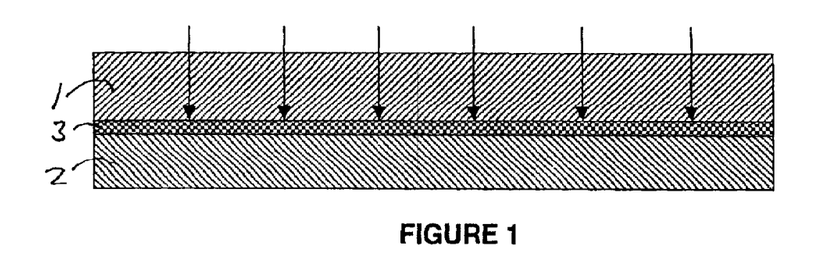
FIG. 1 illustrates, in a side sectional view, a polycarbonate/negative photoresist laminate being subjected to radiation for preparation of the microfluidic device structure shown in FIG. 4.

FIGS. 1 through 4 illustrate the fabrication of a typical microfluidic structure of this invention. A laminate is prepared as shown in FIG. 1, comprising a negative photoresist matrix layer 1 laminated to a support layer 2. Matrix layer 1 is made from SU-8-25, a solvent-based negative photoresist material manufactured by Microlithography, Inc. Support layer 2 is a polycarbonate sheet having a thickness of approximately 500 microns, Support layer 2 has a one half micron sputter coat of gold 3 at the interface with matrix layer 1. This coating was applied during manufacture to protect layer 2 from erosion during the development of matrix layer 1. The matrix layer was prepared by coating the support layer 2, over sputter coat 3, with the solvent-based negative photoresist SU-8 by conventional spin coating techniques, utilizing a conventional resist spin coater, to form matrix layer 1. A spin speed of 300 rpm and a spin time of only 10 seconds are employed in order to obtain the desired thickness for matrix layer 1 of about 600 microns.

Figure 2:
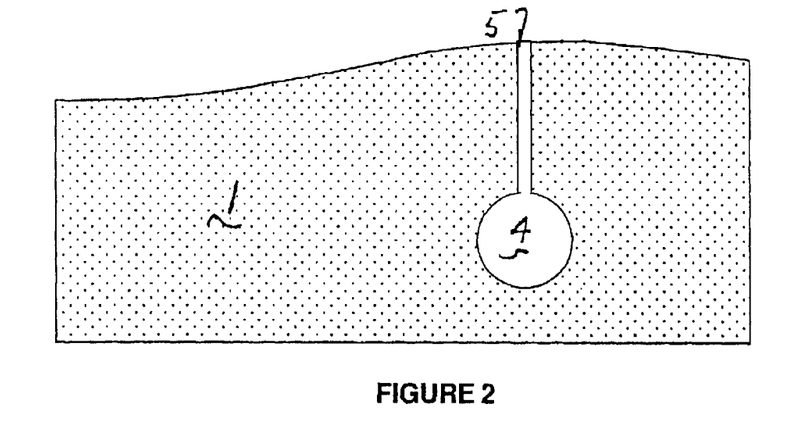
FIG. 2 is a fragmentary top view of the laminate of FIG. 1 after development of the negative photoresist showing the well and connecting channel in the photoresist layer resulting from development.
Figure 3:
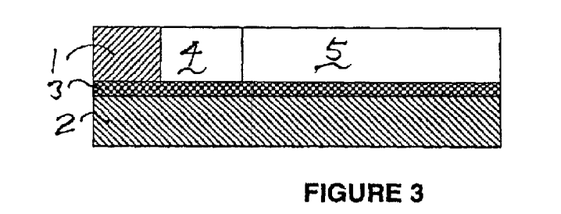
FIG. 3 is a side sectional view taken along lines 2—2 of FIG. 2.
Figure 4:
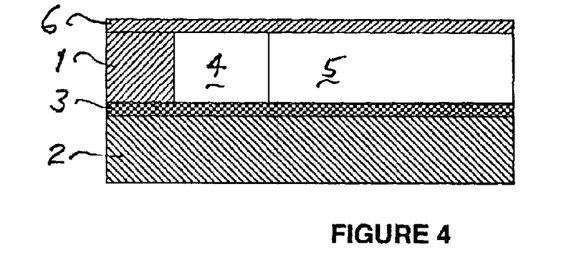
FIG. 4 is the view of the laminate shown in FIG. 3 after a cover layer has been applied on the upper surface to cover the well and connecting channel.

The laminate is subjected to radiation on the matrix layer side, using a photomask having a masked area defining a well and channel. The radiated laminate of FIG. 1 is then developed with 1-methyl-2-propyl acetate to produce the well 4 and connecting microchannel 5 in matrix layer as shown in FIGS. 2 and 3. Microchannel 5 is for connecting well 4 with another microchamber or other element of a microfluidic device in the matrix layer (not shown) or to exterior of the matrix for fluid communication as may be appropriate to the particular device. A cover layer 6 is laminated to the surface of matrix layer 1 opposed to the surface laminated to support layer 2 as shown in FIG. 4. Cover layer 6 closes off microchamber 4 and microchannel 5 at the matrix layer surface. Cover layer 5 is Pyrolux PC1025. The negative photoresist forming matrix layer 1 has been fixed, through exposure to radiation in the manufacturing, to a stable and durable condition.

In the embodiments of FIGS. 5 through 19, two layers of negative resist are employed, with the first serving as the matrix layer for microfluidic devices and the other serving both as the support layer and as a matrix for additional components of the microfluidic devices, such as electrode contacts. These embodiments are particularly important where the fluidic devices are to be sensors as it enables the sensor sites and the electrode contacts to be on opposite sides of the non-silicon substrate. These novel electrode structures may comprise a monolithic substrate having a top opening and a bottom opening facing generally away from each other at the same site. They may be fabricated by a low cost methodology utilizing a dry photoresist film as the substrate layer. Standard photolithography and silk screening may be used in the fabrication process.

Figure 5:
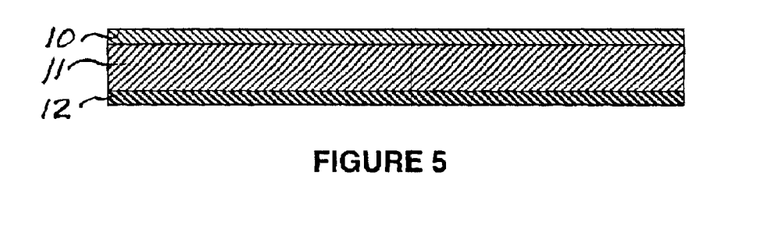
FIG. 5 illustrates, in a side sectional view, a sheet of dry negative photoresist film with a peelable cover sheet on the top side and a peelable cover sheet on the bottom side, as the starting material for fabricating the microsensor structure shown in FIG. 14.

As shown in FIG. 5 the fabrication process may begin with a piece of dry photoresist film (DuPont Pyralux PC1025). This is a flexible negative photo-imageable film It is composed of three layers, a peelable polyolefin release liner or cover sheet 10, the photo developable dry film 11, which will comprise the support layer for the construction, and peelable cover sheet 12, a mylar protective liner or cover sheet. The cover sheets provided protection for the preformed photoresist in its relatively soft and tacky prior to fixing by irradiation.

Figure 6:
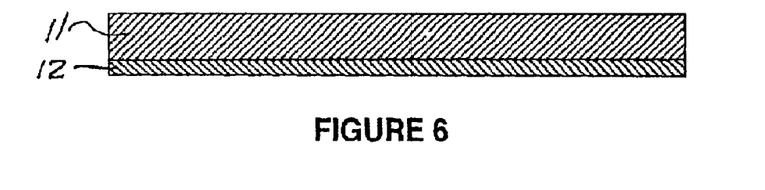
FIG. 6 illustrates the sheet of FIG. 5 with the top cover sheet removed.
Figure 7:
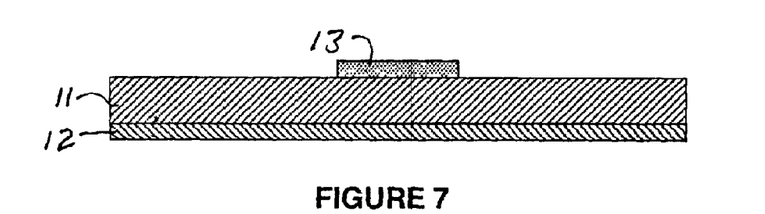
FIG. 7 illustrates the sheet of FIG. 6 with a layer of silver applied to the surface of the sheet.

The cover sheet 10 is removed from the dry photoresist laminate, as shown in FIG. 6. A layer of silver 13 is screen printed, using under yellow light onto the photo-polymer support layer 11 and then cured by a soft bake as seen in FIG.

7. For his purpose a polymer-based silver paste is applied as described at pages 127–128 of *Fundamentals of Microfabrication* referenced above. Silver layer 13 is to serve as the electrode for the sensor and its size and shape is adjustable depending on sensor application needed.

Figure 8:
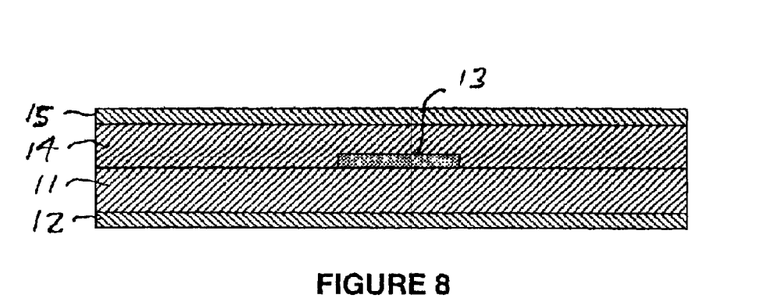
FIG. 8 illustrates the sheet of FIG. 7 with a second dry negative photoresist sheet laminated to the first photoresist sheet, over the silver layer applied thereto.

As seen in FIG. 8, layer 14 of the same dry photoresist film (DuPont Pyralux PC1025) having cover sheet 15, but with the mylar cover sheet removed, is laminated face down over the silver layer to serve as the negative photoresist matrix layer for the microfluidic devices (sensors) in the construction.

Figure 9:
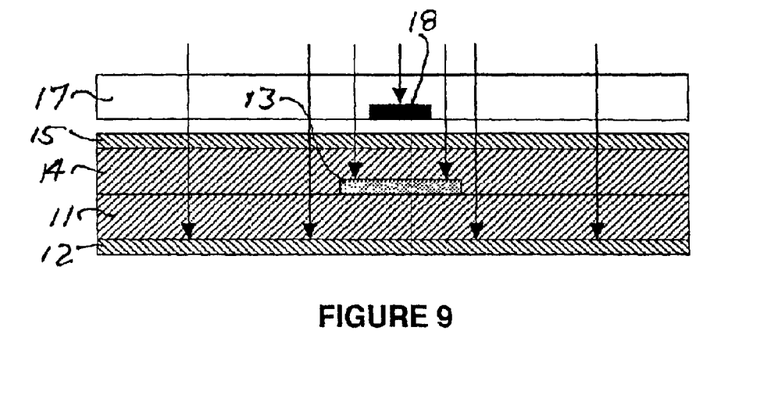
FIG. 9 illustrates the laminate of FIG. 8 being exposed to radiation through a photomask.
Figure 10:
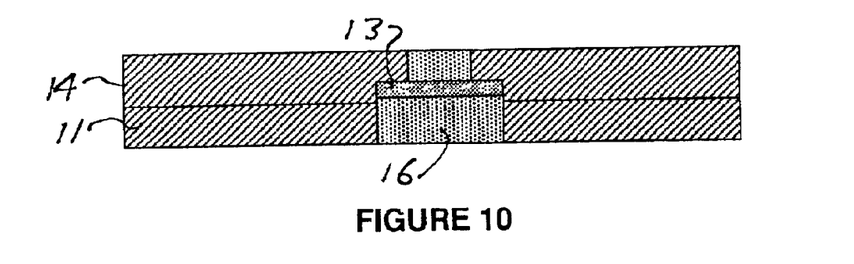
FIG. 10 illustrates the laminate of FIG. 9 showing the exposed and unexposed regions.

Referring to FIG. 9 a transparent plate 17 having a mask 18 smaller in coverage area than silver layer 13 is positioned above photoresist matrix layer 14 with mask 18 aligned directly over silver layer 13. The laminated sheets are exposed under UV light from only one side, through plate 17. The silver layer 13 itself acts as a mask for the dry resist layer underneath it so that, in addition to the area in below mask 18 in photoresist 14, the entire area at 16 in photoresist 11 remains unexposed, as seen in FIG. 10. After exposure the remaining two outer layer cover sheets, coversheets 10 and 15, are removed prior to development.

Figure 11:
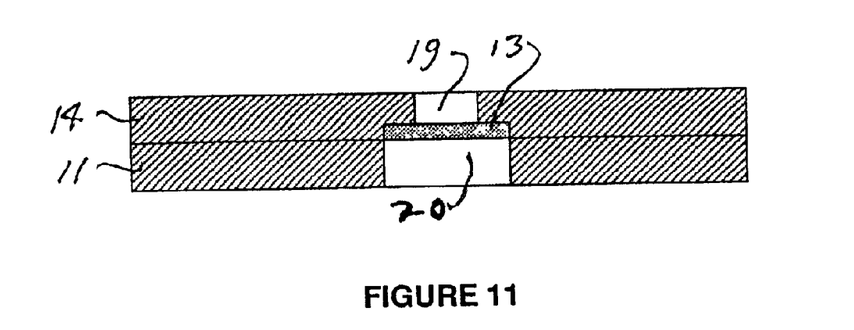
FIG. 11 illustrates the structure of FIG. 10 after developing and rinsing of the photoresist layers.

Both the photoresist constituting matrix layer 14 and the photoresist constituting support layer 11 are then developed leaving a small cavity or well 19 above the silver layer 13 and a larger cavity or well 20 beneath silver layer 13 as seen in FIG. 11.

Figure 12:
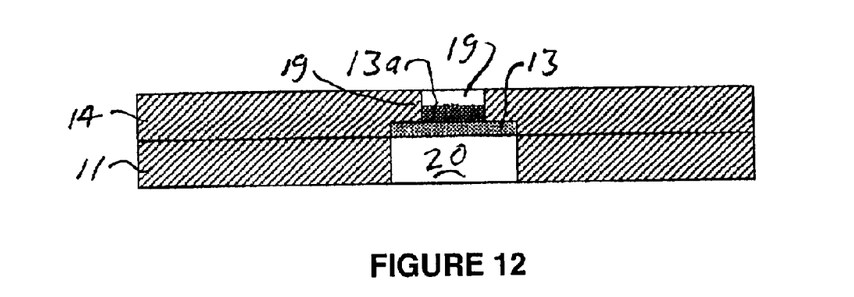
FIG. 12 illustrates the structure of FIG. 11 after chemically converting the surface of the silver layer to silver/silver chloride.
Figure 13:
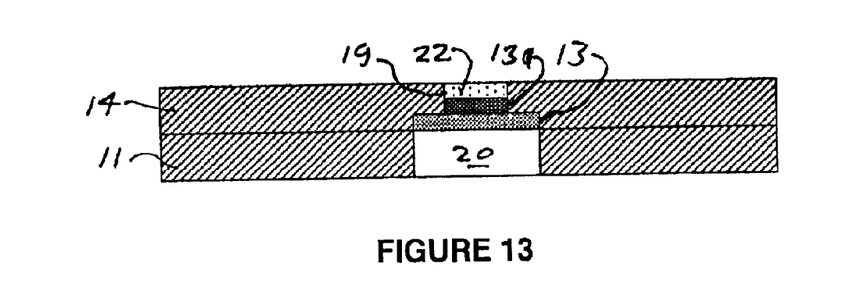
FIG. 13 illustrates the structure of FIG. 12 after deposition of electrolyte medium in the well in the upper (matrix) layer of negative photoresist.

To utilize this microfluidics construction as a sensor the surface 21 of silver layer 13 facing the smaller upper well 19 is chloridized with $FeCl_3$ solution, as shown at 13a in FIG. 12. Upper well 19 is filled with an electrolytic medium 22 as seen in FIG. 13. The electrolytic medium can be a liquid but more preferably is in the nature of a hydrogel or a solid polymer electrolyte.

Figure 14:
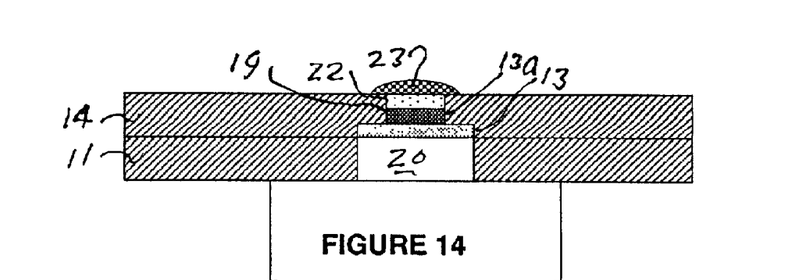
FIG. 14 illustrates the completed sensor structure of FIG. 13 after depositing of a membrane on the upper surface thereof over the well.

After well 19 has been charged with electrolyte medium 22, a membrane 23 is deposited on matrix layer 11 over the top of well 19 to complete the microchamber as seen in FIG. 14. Membrane 23 is a microporous membrane or otherwise contains suitable openings for fluid communication into the microcell created by well 19 as suitable for the particular sensor. A plasticized polymeric membrane is normally used for covering potentiometric elements. Ion-selective membranes may be employed, as appropriate for particular sensors Alternatively, membrane 23 may be applied as a continuous layer over matrix layer 11.

It will be understood that utilizing the foregoing procedure a multiplicity of identical structures may be fabricated at the same time across the surface of the laminate formed from matrix layer 14 and support layer 11. The microfluidic structure and fabrication process is uniquely suitable not only for utilizing photoresists and support webs in cut sheet form but also in roll form. Because flexible materials may be employed in these structures, lamination, irradiation, printing, development and other steps may be carried out efficiently in a continuous process from webs of photoresist, support webs and laminates thereof.

Figure 15:
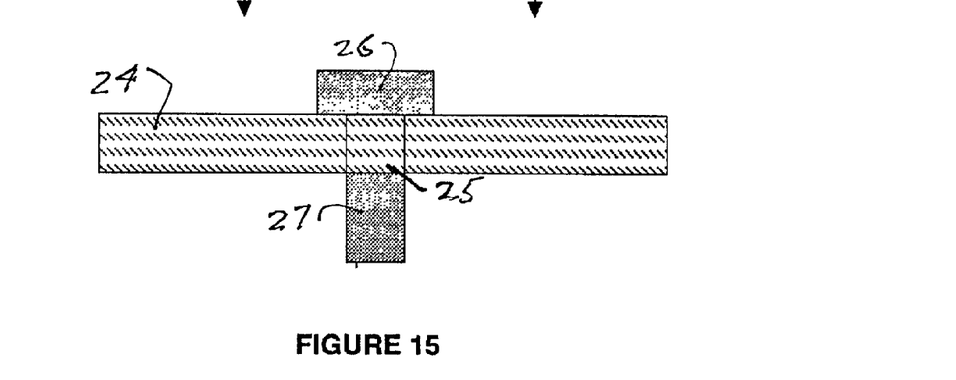
FIG. 15 illustrates a biomodule substrate bearing an electrical contact pin.

After completion, individual sensors may be separated by means of laser cutting, etc. The various sensors, so fabricated, may then be combined as desired into a biomodule array. For this purpose a bio-module substrate 24 as seen in FIG. 15 may be employed. Substrate 24 bears a plurality of spaced electrical contact pins extending through the substrate, such as pin 25. Each pin 25 has a sensor contact plug 26 at one side of substrate 24 and an external contact plug 27 at the opposed side. Plug 26 is sized to fit into well 20 of each sensor. Each completed sensor is placed into the array by mounting the sensor onto a contact plug 26 of the biomodule as shown in FIG. 16.

Figure 16:
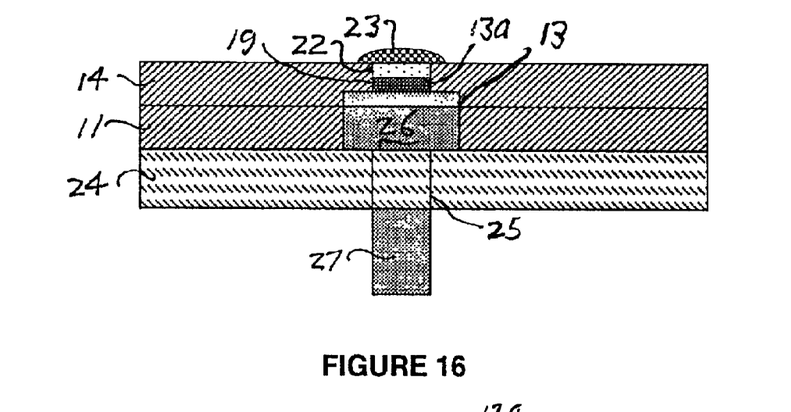
FIG. 16 illustrates the sensor structure of FIG. 10 engaged with the biomodule substrate of FIG. 15.

As best seen in FIGS. 14–16, silver layer 13 and thus well 20 are larger than well 19 in layer 11. Contact plug 26 of the biomodule is of substantially the same size as well 20. Thus when contact plug 26 is inserted into well 20 it will seat against peripheral portions of silver layer 13 that are below layer 14. This arrangement will help to avoid inadvertent penetration of plug 26 through silver layer 13. Alternatively, for the same purpose, silver layer 13 and well 20 may be extended partially or completely outside the perimeter of well 19 so that well 20 is offset from well 19.

By combining different types of sensors onto a biomodule array with pick and place technology instead of fabricating different sensors on the same substrate sheet the yield will increase substantially while the cost per sensor is decreased by up to a factor of ten. This decrease in the cost per sensor comes without any loss of in sensor performance. The bottom opening is used for the sensor's electronics contact so that the sensors can be fabricated upon demand and then placed into various sensor array configurations by pick and place technology.

Figure 17:
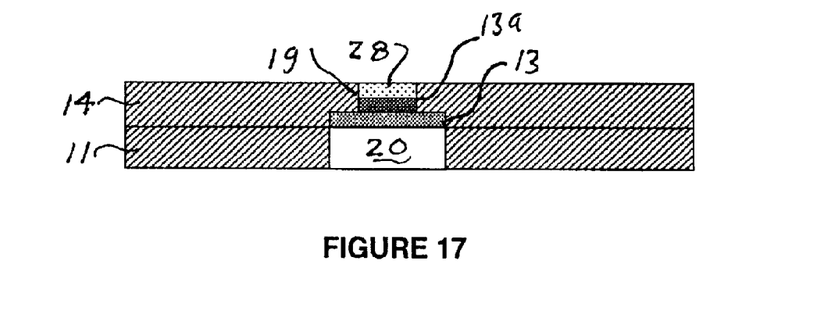
FIG. 17 illustrates the structure of FIG. 12 in which the upper well has been charged with a reference solution for use of the sensor structure as a reference electrode.
Figure 18:
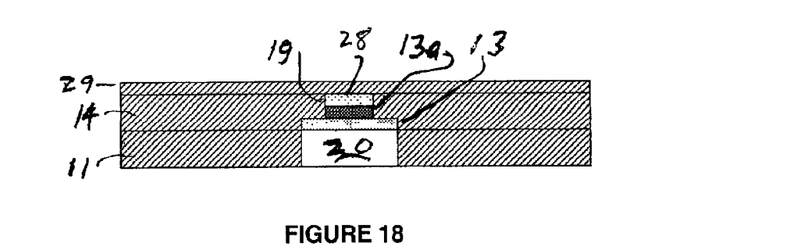
FIG. 18 illustrates the structure of FIG. 17 with a dry negative photoresist laminated on the upper surface and closing off the upper well.
Figure 19:
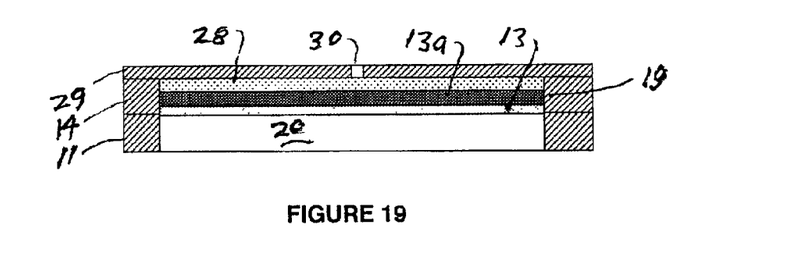
FIG. 19 is an enlarged fragmentary view of the upper well structure shown FIG. 18 with a small hole in the top photoresist layer opened over the upper well, to complete the reference electrode.

The foregoing microfluidic structure may also be employed as a reference electrode. For this purpose well 19 may be charged with a reference solution 28 as seen in FIG. 17. Referring to FIG. 18, continuous negative dry photoresist layer 29 is then laminated onto matrix layer 14 to close off well 19, thus completing the microchamber underneath the layer 29. After this step a small hole 30, similar to a frit, can be formed in layer above well 19 completing the reference electrode, as shown in FIG. 19. This is accomplished by the same procedure used to form well 19. Photoresist layer 19 is exposed to radiation through a photomask having an appropriately small mask over well 19. Layer 29 is then developed to create hole 30.

Figure 20:
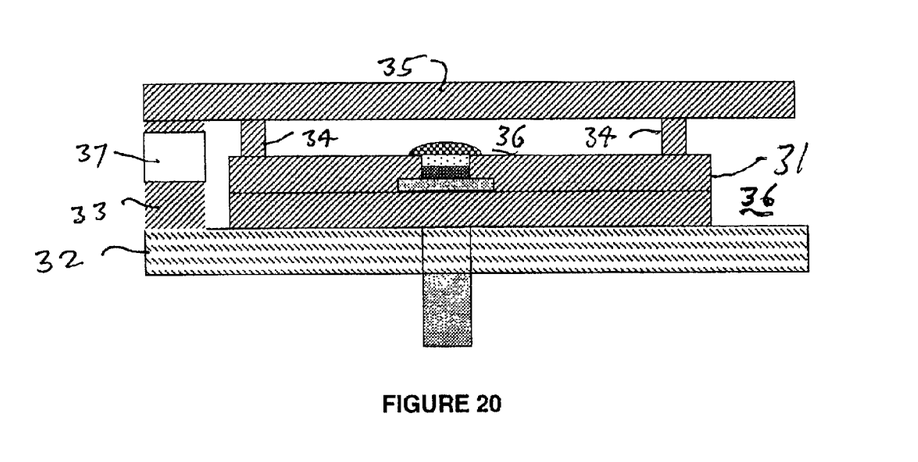
FIG. 20 is a fragmentary side view of a biomodule illustrating a cover structure of this invention.

In the is a fragmentary view of FIG. 20 is shown sensor 31 at one side of a biomodule, which is one of a series of different sensors arrayed on biomodule substrate 32. Substrate 32 bears a wall 33 which is photoresist constructed and fixed on top of the substrate at its perimeter. Pillars 34 are mounted on top of sensor 32 and also may be formed by resist procedure. Cover 35 is a preformed dry negative photoresist which extends across substrate 32. Cover 35 is applied over and bonded to wall 33 and pillars 34 and is then fixed by radiation. Both wall 3 and pillars 34 extends a distance above sensor 32 forming a bridge to leave a chamber 36 between cover 35 and substrate 32 for fluid communication to and between the sensors on the substrate. A port 37 is provided in wall 33 for fluid communication from the outside into chamber 36. This structure is particularly suitable for analyzing biological fluids such as blood.

This invention eliminates the expensive IGA process and bonding but still has the main LIGA-type advantages. By this invention, a large number of identical planar sensors can be made on a separate substrate (the photoresist laminate), and each laminate sheet contains only one type of sensor (e.g. K+, O2, and reference electrode). This will increase the yield and reduce process incompatibilities so that the cost per sensor is very low compared to previous sensor fabrication methods. Sensors of different types can then be cut from different resist sheets and combined in any desired array by pick and place technology.

Although the description above contains many specificities, these should not be construed as limiting the scope of the invention but as merely providing illustrations of some of the presently preferred embodiments of this invention. Various other embodiments and ramifications are possible within it's scope.

What is claimed is:

1. A method for forming a planar microfluidic device which comprises:
   a. forming a laminate structure comprising a negative photoresist matrix layer and a non-silicon planar substrate layer,
   b. forming on the matrix layer side of the laminate a radiation resistant mask over at least one area defining a desired cavity in the matrix layer,
   c. exposing the matrix side of the laminate structure to radiation to render the exposed portions resistant to etching,
   d. developing the matrix layer to form a cavity extending into the laminate structure from the matrix layer side to the interface and
   e. laminating to the laminate structure on the matrix side a membrane layer covering the cavity, whereby to form a chamber in the structure.

2. A method as in claim 1 and wherein the negative photoresist matrix layer is formed by laminating to the substrate a preformed negative photoresist sheet.

3. A method as in claim 2 and wherein the negative photoresist sheet is a film.

4. A method as in claim 1 and wherein the membrane laminated on the matrix side of the laminated structure is a negative photoresist which after lamination thereof is exposed to radiation on the side of the membrane remote from the matrix layer to thereby fix the membrane and bond the membrane to the matrix side of the laminated structure.

5. A method as in claim 4 and wherein, prior to fixing the membrane, a radiation resistant mask is formed over the membrane on the side of the membrane remote from the matrix layer at at least one area defining a desired hole in the membrane that is aligned with the cavity and, following exposure of the membrane to radiation, the membrane is developed to etch a passage through the membrane for fluid communication with the cavity in the matrix layer.

6. A method as in claim 1 and wherein the planar substrate layer comprises a negative photoresist, a radiation-opaque electrode is formed on the matrix layer side of the planar substrate layer prior to formation of the laminate structure, the mask is aligned with the electrode and covers a portion thereof and the substrate layer is developed, whereby to etch a larger well beneath the electrode extending through the substrate layer.

7. A method of constructing an electrochemical cell comprised of a laminated film substrate, comprising:
   a. forming a radiation-opaque electrode on a first surface of a first flexible negative photoresist,
   b. laminating a second flexible negative photoresist to the first photoresist at the first surface of the first photoresist, thereby forming an interface between the first and second photoresists at the first surface of the first photoresist,
   c. forming a mask on the side of the second photoresist remote from the interface between the first and second photoresists that aligned with the electrode and covering a portion thereof,
   d. exposing the second photoresist to radiation from the side opposed to the interface between the first and second photoresists,
   e. developing the photoresists, whereby to etch a well through the second photoresist to the electrode and a larger well beneath the electrode, extending through the first photoresist.

8. A method as in claim 7 and including the step of laminating to the second photoresist on the side of the second photoresist remote from the interface between the first and second photoresists a membrane layer covering the well in the second photoresist whereby to form a fluid barrier to the exterior of the well.

9. A method as in claim 8 and wherein the membrane laminated to the second photoresist is a negative photoresist which after lamination thereof is fixed by exposure to radiation on the side of the membrane remote from the interface between the first and second photoresists.

10. A method as in claim 9 and wherein, prior fixing the membrane, a radiation resistant mask is formed over the membrane on the side of the membrane remote from the interface between the first and second photoresists at at least one area defining a desired hole in the membrane that is aligned with the well and, following exposure of the membrane to radiation, the membrane is developed to etch a passage through the membrane for fluid communication with the well in the second photoresist.

* * * * *